US008304717B2

United States Patent
Renner

(10) Patent No.: US 8,304,717 B2
(45) Date of Patent: Nov. 6, 2012

(54) MEASUREMENT OF ION MOBILITY SPECTRA

(75) Inventor: Uwe Renner, Leipzig (DE)

(73) Assignee: Bruker Daltonik GmbH, Bremen (DE)

( * ) Notice: Subject to any disclaimer, the term of this patent is extended or adjusted under 35 U.S.C. 154(b) by 309 days.

(21) Appl. No.: 12/407,511

(22) Filed: Mar. 19, 2009

(65) Prior Publication Data

US 2009/0236514 A1     Sep. 24, 2009

(30) Foreign Application Priority Data

Mar. 19, 2008 (DE) .......................... 10 2008 015 000

(51) Int. Cl.
*B01D 59/44* (2006.01)
(52) U.S. Cl. ....................................... 250/286; 250/282
(58) Field of Classification Search .................. 250/282, 250/286
See application file for complete search history.

(56) References Cited

U.S. PATENT DOCUMENTS

| 4,633,083 | A |   | 12/1986 | Knorr et al. | |
|---|---|---|---|---|---|
| 4,707,602 | A |   | 11/1987 | Knorr | |
| 4,755,670 | A | * | 7/1988 | Syka et al. | 250/292 |
| 4,959,543 | A | * | 9/1990 | McIver et al. | 250/291 |
| 5,396,065 | A |   | 3/1995 | Myerholtz et al. | |
| 5,719,392 | A |   | 2/1998 | Franzen | |
| 6,198,096 | B1 |   | 3/2001 | Le Cocq | |
| 6,483,109 | B1 | * | 11/2002 | Reinhold et al. | 250/292 |
| 6,580,068 | B1 |   | 6/2003 | Tarver, III et al. | |
| 6,782,342 | B2 |   | 8/2004 | LeGore et al. | |
| 6,787,762 | B2 | * | 9/2004 | Tarver et al. | 250/286 |
| 7,417,222 | B1 | * | 8/2008 | Pfeifer et al. | 250/282 |
| 2005/0058218 | A1 | * | 3/2005 | Jenkins | 375/295 |
| 2006/0226357 | A1 | * | 10/2006 | Franzen et al. | 250/307 |
| 2007/0143081 | A1 | * | 6/2007 | Goldberg | 702/191 |
| 2009/0032696 | A1 | * | 2/2009 | Dahl et al. | 250/282 |
| 2010/0084549 | A1 | * | 4/2010 | Ermakov et al. | 250/283 |

FOREIGN PATENT DOCUMENTS

WO     WO2004/102178     11/2004

OTHER PUBLICATIONS

Knorr et al. "Fourier Transform Ion Mobility Spectrometry", Anal. Chem 1985, col. 57, pp. 402-406.

* cited by examiner

Primary Examiner — Michael Logie
(74) Attorney, Agent, or Firm — O'Shea Getz P.C.

(57) ABSTRACT

The invention relates to measuring the mobility spectra of ions with ion mobility spectrometers (IMS). The invention provides an analog modulation of the ion current of an IMS ion source with a continuous modulation function, the instantaneous frequency of which temporally varies across a large frequency range, and a generation of the mobility spectrum from the measured ion current by a correlation analysis with the modulation pattern. The modulation can, for example, be produced by the gating grid, which is usually present. The analog modulation removes many of the difficulties which occur with square-wave modulation and leads to a surprisingly stable evaluation which is relatively insensitive to noisy signals and produces a high mobility resolution at very low noise.

9 Claims, 2 Drawing Sheets

MEASUREMENT OF ION MOBILITY SPECTRA

PRIORITY INFORMATION

This patent application claims priority from German patent application 10 2008 015 000.2 filed Mar. 19, 2008, which is hereby incorporated by reference.

FIELD OF THE INVENTION

The present invention relates to the field of ion mobility spectrometry and in particular to a method for measuring the mobility spectra of ions with an ion mobility spectrometer (IMS).

BACKGROUND OF THE INVENTION

Ion mobility spectrometers are usually operated by injecting short ion current pulses into the drift tube. The ions are continuously generated in an ion source and then admitted into the drift region of the spectrometer by a gating grid over a short time span. The time spans for the admission usually amount to between 100 and 300 microseconds; the acquisition of the spectrum takes about 30 milliseconds. Bipolar grids are used as gating grids.

The ions admitted by the grid are drawn through a collision gas in a drift region by an axial electric field. The velocity of the ions depends on their "mobility", which, as known, in turn depends on their collision cross-section, their mass, their polarizability and their tendency to form complex ions with molecules from the collision gas. In the ion source, several ion species, such as monomers, dimers and complexes with water and with the collision gas, are usually formed from the molecules of a substance. Every ion species has a characteristic mobility. At the end of the drift region, the incident ion current is measured at an ion detector, digitized and stored as a "mobility spectrum" in the form of a digitized sequence of measured ion current values. An evaluation of this mobility spectrum provides information on the mobilities of the ions involved and therefore indications for the substances involved.

The method is sensitive to certain groups of substances and is used on a large scale in the measurement of pollutants in air, for example, for monitoring chemical laboratories, continuous monitoring of filters, control of drying processes, monitoring of exhaust air, detecting warfare gases, and so on.

Ions with the same charge experience the same drawing force from the electric field, but as a result, ions with different collision cross-sections and different masses have different drift velocities through the collision gas. For lighter ions of about the mass of the collision gas, their mobility is determined mainly by the reduced mass of the ions, for heavier ions from several hundred or thousand atomic mass units upward, it is the particular form of the molecule that is decisive and the collision cross-section becomes significant.

The switching operation of the grid acts as the start time for measuring the drift velocity of the different bunches of ions. During the drift process, the diffusion of the ions in the forward and backward direction generates a diffusion profile for each bunch of ions containing ions of the same mobility. This results in a roughly Gaussian bell-shaped curve for the ion signals. The drift velocity is determined from the measured drift time in the center of the bell-shaped curve and the known length of the drift region in the drift tube of the spectrometer.

The ions of the analyte substances are regularly formed by so-called "atmospheric pressure chemical ionization" (APCI) in reactions with reactant ions by protonation or deprotonation, and dimeric ions and complexes involving water and collision gas molecules are formed in addition to monomeric pseudomolecular ions. "Pseudomolecular ions" are protonated or deprotonated analyte molecules and therefore have a mass that is increased or reduced by one atomic mass unit compared to a normal molecular ion. The ratios of the individual ion species with respect to each other depend on the concentration of the analyte molecules in the collision gas.

Nitrogen or air is usually used as the collision gas. The collision gas contains traces of water vapor, the concentrations of which are usually carefully controlled by filter units. The primary reactant ions are in most cases generated by irradiation from beta emitters, for example 63Ni, but corona discharges and other electron beam generators and UV lamps are also used for this purpose. The secondary reactant ions are formed in a reaction chain, which starts with the production of primary nitrogen ions and ends up with a number of different water complex ions. These water complex ions perform the actual chemical ionization of the analyte molecules by protonation or deprotonation.

As the analyte ions drift through the collision gas of the drift region, the ions quickly experience new attachments and losses of H2O water molecules and N2 nitrogen molecules. Statistically averaged, an analyte ion, whether it is a monomer or a dimer, thus contains a×H2O and b×N2, where a and b are usually non-integral numbers. The peak in the mobility spectrum is hardly broadened by this because these changes happen very quickly in a kind of dynamic equilibrium. If one investigates the ions of such a peak in a connected mass spectrometer, one freezes a momentary state, just like in a flash photograph, and obtains a mass spectrum which contains the ions with various states of attachment, and thus very different masses, side by side.

For a conventional repetition rate of the spectrum measurements of about 30 spectra per second, and an ion gating time of between 150 and 300 microseconds, the utilization factor of the ions of a substance introduced in a gaseous state amounts to only between a half and one percent. The remaining ions are discharged, predominantly in the gating grid, and are lost for any further measurement.

Ion mobility spectrometers are often compared to time-of-flight mass spectrometers because both are spectrometers with a time-of-flight dispersion. There are, however, major differences, which mainly concern the diffusion of the ions in the collision gas and thus the shape of the ion signals at the detector. Despite the large differences, some publications dealing with the evaluation of either time-of-flight mass spectra or mobility spectra are discussed here.

F. J. Knorr et al. (Anal. Chem. 1985, 57, 402; U.S. Pat. No. 4,633,083) have discussed a technique that operates in a time-of-flight dispersion spectrometer with an axial ion beam that is modulated by two barrier grids. According to the diagrams, the modulation function used is a square-wave function, i.e., an alternating complete closing and complete opening of the grid (a "binary function"). The first barrier grid is positioned directly behind the ion source, the second directly in front of the ion detector. Synchronous frequency modulation of both grids generates an interference value for the ion beam at which some ion species can pass through, while others are kept back by the interference of their drift time with the phases of the grid voltages. If this modulation frequency is altered, an interference spectrum ("interferogram") can be acquired, which can be transformed by a Fourier transformation from the frequency domain of the interferogram into the time domain and thus into a mobility spectrum. The method, which has been called "Fourier Transform Ion Mobility Spectrometry" by its authors, offers a theoretical ion utilization factor of 25 percent because the ion quantities are halved at each of the two grids. However, expectations for this method in terms of increasing the signal-to-noise ratio have been disappointing, and the method has not gained acceptance up to now.

In U.S. Pat. No. 4,707,602 by F. J. Knorr, the second grid is replaced by a modulation of the detector current, or even modulation of the flow of the measured data, in order to generate the interference signal. Here, a square-wave modulation is shown in the diagrams, while the description also refers to a sinusoidal modulation. The utilization factor for the ions from the ion source is again 25 percent.

In order to produce clean interferograms with the two methods mentioned above, the modulation frequency must practically not vary during the time the ions drift from the first gating grid to the second gating grid or to the detector. This necessitates a slow change of the modulation frequency.

U.S. Pat. Nos. 5,396,065 and 6,198,096 disclose techniques for time-of-flight mass spectrometers (i.e., not for ion mobility spectrometers) which operate with very short pulses of ions. These pulses are stochastically distributed, with respect to time, with as high a density as possible so that the mass spectra of the pulses strongly overlap. The pre-determined pattern of the pulses forms a pseudo-stochastic sequence. The detector signal with the strongly overlapping mass spectra is evaluated by a correlation with the pattern of electric pulses at the gating grid, resulting in a well-resolved mass spectrum. In contrast to the patents described above, this method uses only one modulator for the ion current, a gating mechanism which only allows the passage of ions for a short time in the order of a few nanoseconds, and uses a correlation procedure to decode the ion current. It should be noted that a time-of-flight mass spectrometer does not have any diffusion broadening of the ion packages and that the detector signal is a simple superposition of the mass spectra of the individual ion pulses.

U.S. Pat. No. 5,719,392 discloses the ion current of an ion mobility spectrometer is modulated by the gating grid with a square-wave temporal Hadamard pattern, where both the pulse width of the admitted ion packages as well as their separations are statistically distributed. The evaluation to obtain the mobility spectrum can be done by either using a cross-correlation of the detector current and the impressed pattern, or by using Fourier or Hadamard transformations. Using the Fourier transformation makes it possible to obtain an improved mobility resolution by a partial deconvolution with the apparatus function. It has become apparent, however, that this evaluation procedure using the Fourier transformation does not operate stably for a noisy detector signal.

A cross-correlation in conjunction with a binary switched Hadamard pattern in a time-of-flight mass spectrometer is also used in U.S. Pat. No. 6,782,342.

U.S. Pat. No. 6,580,068 discloses an embodiment of the above-cited U.S. Pat. No. 4,707,602 expanded to all time-dispersive spectrometers. The modulation of the detector current, at least, has the function of a fast switch, and is thus binary, having the two states: admit and block. According to the authors, the modulation of the ion current of the ion source shall have the same shape, where possible, i.e., shall also be binary modulated. This patent cites a "chirp", i.e., a temporal change of the modulation frequency from low to high frequencies, but uses only transformations of the interferogram from the frequency domain into the time domain and does not use cross-correlations.

There is a need for an improved technique of measuring the mobility spectrum of ions.

SUMMARY OF THE INVENTION

According to an aspect of the present invention, the ion current from the ion source is analog-modulated with a continuous modulation function (e.g., a sine function) with an instantaneous modulation frequency varying over a frequency range. The resulting ion current signal is decoded at the detector by a correlation with the modulation function. The modulation function may be a linear or nonlinear chirp.

Advantageously, the method generates a relatively noise-free mobility spectrum with good mobility resolution.

As can be seen from FIG. 2, the gating grid of a commercial ion mobility spectrometer may be used for the analog modulation; it even creates fewer problems than the operation with fast switching on and off that is required for a square-wave modulation. The analog modulation may be defined as "continuous" if the voltage increase or decrease is less than one volt per hundred microseconds.

It is preferable to vary the modulation frequency in a single chirp, which is conducted from the lower frequency limit of zero hertz up to an upper frequency limit, and is extended over the chosen measuring time. The upper frequency limit determines the maximum mobility resolution. An upper frequency limit of seven kilohertz results in peak widths at half-maximum height of about 200 microseconds. A "linear chirp" $[\sin(\omega 0(t-t0))t]$ is preferred, with a linear frequency increase $\omega = \omega 0(t-t0)$ over time t. The modulation control signal for the gating grid may be generated by a digital-to-analog conversion of pre-calculated values of the modulation function, which are stored in a memory for this purpose. The sampling rates for the digital-to-analog conversion of the modulation control signal and also for the analog-to-digital conversion of the ion current from the detector must be fast enough and should be at least some five times the upper frequency limit. The bandwidth of the amplification and the bit resolution of the digital conversion must be higher than with a pulse-operated ion mobility spectrometer because the ion currents with different frequency components can superimpose themselves and the electronics must be protected from saturation.

On a statistical average, 50% of the ions are admitted if the modulation is fully applied between zero ion current and fall ion current. The variation of the modulation frequency in the chirp preferably begins at zero hertz and extends to about seven kilohertz. This modulation affects all ion species; the patterns impressed onto the individual ion species shifting against each other due to the different drift velocities as the ions drift through the drift tube of the mobility spectrometer, so that the ion current at the ion detector displays a complicated overlapping pattern. The temporal sequence of the ion current is measured at the end of the drift region, then digitized and stored. This stored signal pattern can then be decoded by a correlation with the modulation function, and the mobility spectrum of the ions can thus be obtained.

The mobility spectrum thus obtained is a smooth curve with a high mobility resolution that can only be obtained by the conventional pulse method using very narrow pulse widths of less than one hundred microseconds. But the pulse method produces strong noise on the peaks of the mobility spectrum, particularly with such narrow pulse widths, which is not the case with the modulation method according to the invention. The signal-to-noise ratio is improved by a factor of five at roughly the same mobility resolution; this also improves the detection sensitivity by a factor of five.

These and other objects, features and advantages of the present invention will become more apparent in light of the following detailed description of preferred embodiments thereof, as illustrated in the accompanying drawings.

DETAILED DESCRIPTION

Figure 1:
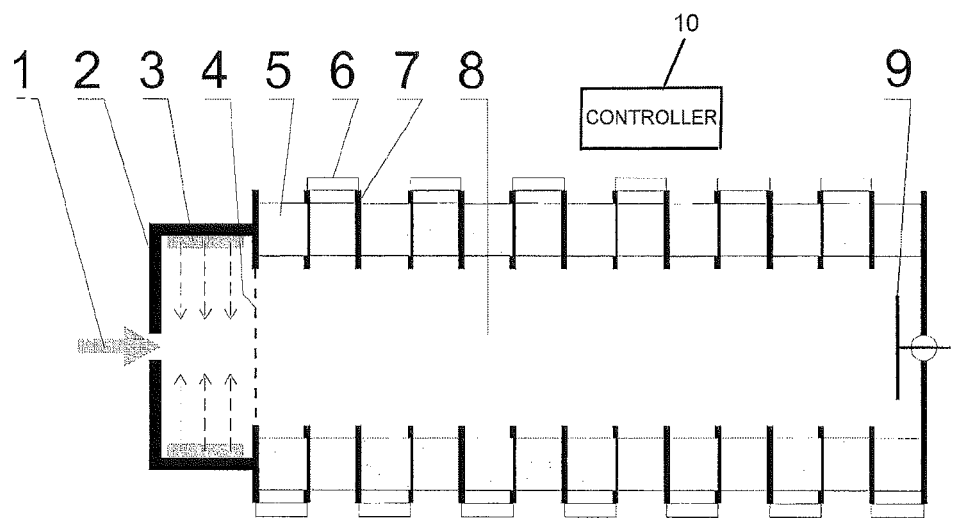
FIG. 1 is a schematic illustration of an ion mobility spectrometer. The schematic representation does not show the internal flow of the collision gas. Air with small traces of water and also substances for analysis contained therein (for example pollutants in the air) enter the ion source housing 2 with the air stream 1. Some air molecules are ionized by the electrons of the beta emitter 3, which includes 63Ni, for example, and react immediately in a complex way with water molecules to form complex ions, which generally have one of the forms (H2O)n. OH3+ or (H2O)n. OH—. These act as reactant gas ions for the ionization of the pollutants by protonation or deprotonation. The ions in the ion source 2 drift toward the gating grid 4; the ion current is analog-modulated here by the modulation function. The drift region 8 includes a plurality of electrodes 7, which are separated from each other by insulators 5. A voltage divider that includes individual resistors 6 supplies them with potentials that generate a uniform electric field in the drift region 8. The ions are pulled by this field and drift through the drift region 8 to the Faraday collector 9, where the ion current is measured versus time.

Referring to FIG. 1, a system of the present invention analog-modulates the ion current from the ion source with a continuous modulation function with an instantaneous frequency varying over a wide frequency range, and decodes the resulting ion current signal at the detector by a correlation with the modulation function. This results in a relatively noise-free mobility spectrum with good mobility resolution. The modulation function may be a linear or nonlinear chirp. The evaluation procedure is extraordinarily stable.

This type of modulation (from the Latin "modulari"—to measure, control, regulate) differs from the modulation familiar from communications technology, which is used to modulate the amplitude, frequency or (more rarely) phase of a generally high-frequency carrier signal with a transported signal. The signal is then contained in the amplitude changes, in the frequency changes or (usually for digital signals only) in the phase shifts of the high-frequency carrier. The ion current which is modulated here originally has neither phase nor frequency; only the modulation function which modulates the ion current between zero and full current has phases and frequencies. Here, the modulation function, which actually corresponds to the transported signal of communications technology, is a coding, which subsequently allows the partial ion currents with ions of different mobilities contained in the ion current to be recognized by the modulation pattern.

This does not mean, however, that the modulation frequency itself may not have a frequency or phase modulation impressed onto it. The designation "continuous modulation function with varying instantaneous frequency" should therefore not be interpreted narrowly. It is contemplated that all conceivable forms of the design of the modulation function shall be included here, as long as the modulation function remains continuous.

The method of the present invention may be used in the instrument illustrated to FIG. 1. The gas flows in ion source and drift region are not depicted here. The substances being analyzed, usually pollutants in air, enter the housing 2 of the ion source in direction 1. The primary nitrogen and oxygen ions generated by a beta emitter 3, for example 63Ni, react in complex reactions initially with water molecules to form the secondary reactant ions described above. These react by protonation or deprotonation with the pollutant molecules. The ions of the pollutants and the remaining reactant ions are conveyed to the gating grid 4 by a slow gas flow. In practice, the slow ion flow thus produced has a diameter of about 5 millimeters. This ion flow then passes through the gating grid 4, which for conventional pulse operation either admits the ion flow or blocks it, with pulse lengths of between about 100 and 300 microseconds.

The gating grid 4 includes a transparent grid of closely arranged pole wires, which can be alternately supplied with different potentials. The ions are thus drawn to the wires, where they are discharged and the ion current is blocked. If the potentials are removed, the grid 4 is switched to admission; the ions enter the drift region 8 and are pulled through the drift region by the electric field. The electric drawing field is generated by the electrodes 7, which are supplied with the required potentials by a chain of resistors 6. The electrodes 7 are separated by ceramic insulators 5. The drift region 8 usually has a weak opposing gas stream, but the velocity of the gas stream is so low compared to the drift velocity that it usually can be neglected. The gas stream and its generation are not shown here.

The ions admitted to the drift region 8 drift with their own characteristic velocity through the drift tube, which is about 10 centimeters long, to the ion detector 9, where they are measured as ion currents. The detector 9 is constructed as a simple collector plate in order not to impress any additional time smearing, and acts as a Faraday collector. The function of the ion current versus time is termed "ion current signal" below. The ion currents arriving at the detector 9 are amplified, digitized and electronically stored as digitized ion current signals in the familiar way as successive rows of values.

In the normal operating mode of an ion mobility spectrometer, the ions are admitted by the gating grid 4 for only a very short duration of between about 100 and 300 microseconds, and the complete mobility spectrum is measured directly at the detector 9 for a duration of about 30 ms. To improve the signal-to-noise ratio, the process is repeated sufficiently often, for example 30 times, and the spectra acquired are added together, resulting in a total measurement time of approximately one second.

Figure 2:
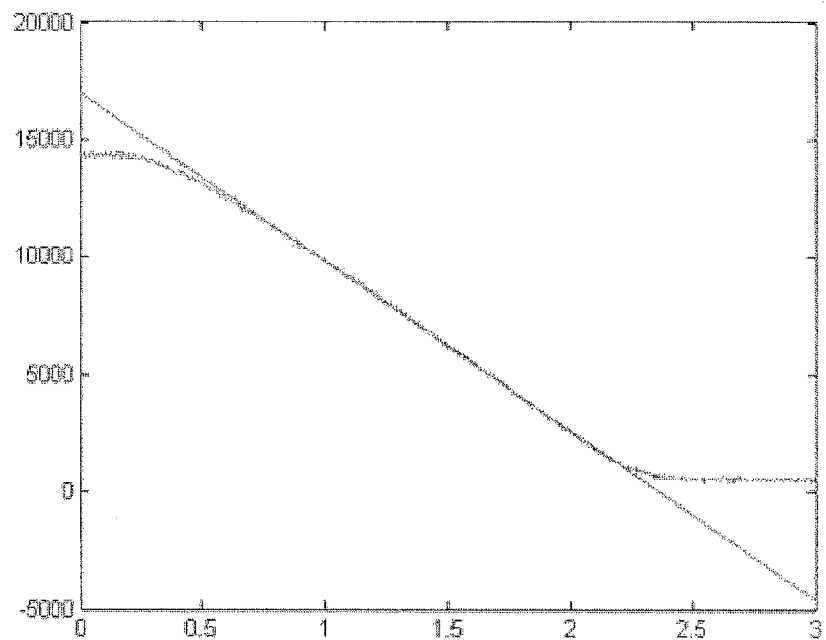
FIG. 2 illustrates the measured ion current in nanoamperes (ordinate) as a function of the control voltage in volts (abscissa) at the gating grid. The curve shows a broad linear operating range suitable for a modulation.
Figure 3:
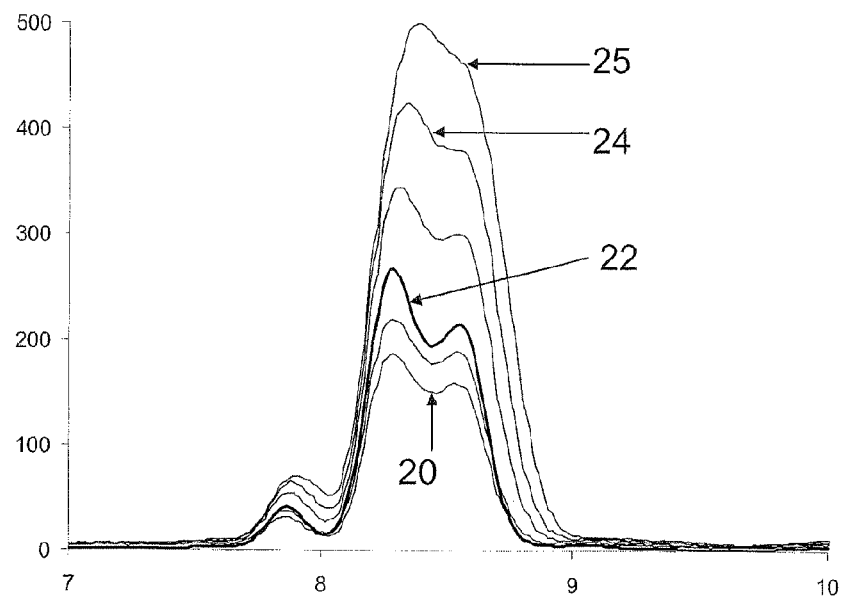
FIG. 3 illustrates the ion mobility spectrum in the region of the reactant ions for the modulation method according to an aspect of the invention (Curve 22) in comparison with prior art pulse methods with pulse widths of between 80 microseconds (Curve 20) and 240 microseconds (Curve 25). Notably, resolution and lack of noise of Curve 22 are significantly improved over the prior art. The abscissa gives the drift times in milliseconds.

In a particularly advantageous mode of operation according to an aspect of the invention, the gating grid 4 is now not operated in binary mode with the two switch states "on" and "off", but this gating grid 4 is used to impress an analog modulation onto the ion current using a modulation function with continuous values. A controller 10 controls the application of the necessary signals for the gating grid to achieve the analog modulation, and processes the detected current signal to obtain the mobility spectrum. The conventional gating grid 4, which has only been used to switch between the two binary limiting states, is quite suitable for this. FIG. 2 shows that the gating grid has a very good, largely linear characteristic for analog control.

Up to now, the development of such gating grids has been directed toward the generation of clean, short ion current pulses. There must be no overshooting of the blocking voltage, especially when the barrier potential is removed because, otherwise, a disadvantageous oscillatory structure would be impressed onto the ion current pulses. Moreover, care must be taken that the ions can pass through the grid as soon as the blocking voltage is removed. These characteristics are now advantageous to the analog control.

The modulation with the continuous modulation function with varying instantaneous frequency does not necessarily have to be done by the gating grid 4, however. The ion generation itself, for example, can be modulated, something which is possible for some types of ion generation such as photoionization, for example. The drift voltage present in the ion source itself can also be controlled appropriately. Unlike the setup shown in FIG. 1, most ion sources also have electrodes 7 and insulators 5 also in the ion source which makes the ions drift towards the gating grid 4. An analog modulation can also be achieved by applying a voltage to these electrodes.

In order to be able to carry out a good correlation evaluation of the ion current signal according to an aspect of the invention, the modulation frequency needs to be suitably varied following a time function. "Chirps" have proven to be particularly advantageous for this. A chirp is a continuous function with a phase function that varies slowly in time compared to the amplitude function. The modulation frequency thus varies monotonically from a lower frequency limit to an upper frequency limit. A linear chirp is a function where the frequency increases (e.g., linearly) with time. It is particularly advantageous if the chirp is extended so that the pre-chosen measuring time, for example one second, is completely filled.

Well-proven in practice is a linear chirp whose lower frequency limit is zero hertz and whose upper frequency limit extends to about seven kilohertz. On the one hand, the upper frequency limit determines the maximum possible mobility resolution of the mobility spectrum obtained from the correlation; on the other hand, the upper frequency limit has a smoothing effect on the mobility spectrum. In a preferred method, the upper frequency limit is adjusted to the maximum mobility resolution, whereby the latter is fundamentally limited by the diffusion broadening. At the same time, the noise in the mobility spectrum which has a frequency above the upper frequency limit disappears. To suppress so-called "side lobes", an amplitude modulation can additionally be impressed on the linear chirp, or the frequency can be corrected in a nonlinear way.

The modulation frequency can, of course, also start at high frequencies and run toward lower frequencies by a reversed chirp. Other modification functions can also be used, including periodic functions or functions which are run several times. It is also possible to use wavelets for a fractal modulation, for example. Periodic modification functions, such as chirps which are run several times, involve the danger that artifacts originating from randomly periodic ion current signals can appear in the evaluated mobility spectrum. The simultaneous use of amplitude and phase modulation expands the possibilities of the modulations in a general way.

The analog modulation method described can be expanded by using codes to change the phase function or the frequency in a continuous and a non-continuous way. In particular, pseudorandom codes (e.g., as produced by Galois fields) can be used to bring about a phase change. The phases can be switched according to a coding, for example between two sinusoidal wave oscillations phase-shifted by 180°, advantageously during zero crossover, which has been tried in practice. Polyvalent codes, for example so-called Costas arrays, can be used for the frequency coding, where the frequency switch occurs during zero crossover of a partial oscillation, leaving the modulation function continuous.

The ion current measured with the detector is usually fed into an amplifier, where it is amplified and then changed into a series of digital measurement values by a digitizer unit. These are then stored in an electronic memory. The amplified ion current will here be called the "analog ion current signal", and the digitally stored series of values will be referred to as the "digital ion current signal".

The correlation of the ion current signal with the modulation function can be carried out both with the analog ion current signal in an electronic correlator, and with the digital ion current signal in a suitable computer. This requires the modulation function to have an auto-correlation function that localizes well. By correlating the measured signal with the modulation signal, the best signal-to-noise ratio can be obtained in the ideal case, i.e., without diffusion losses, according to the so-called "matched filter" theory. It is assumed here that the method of correlation is known, and therefore it is not described further. The result of the correlation procedure carried out on the ion current signal with the modulation function is then the mobility spectrum, which, in the first case, is obtained as an analog spectrum, in the second as a digital spectrum. To evaluate it further in a computer, the analog mobility spectrum must also be digitized.

Figure 4:
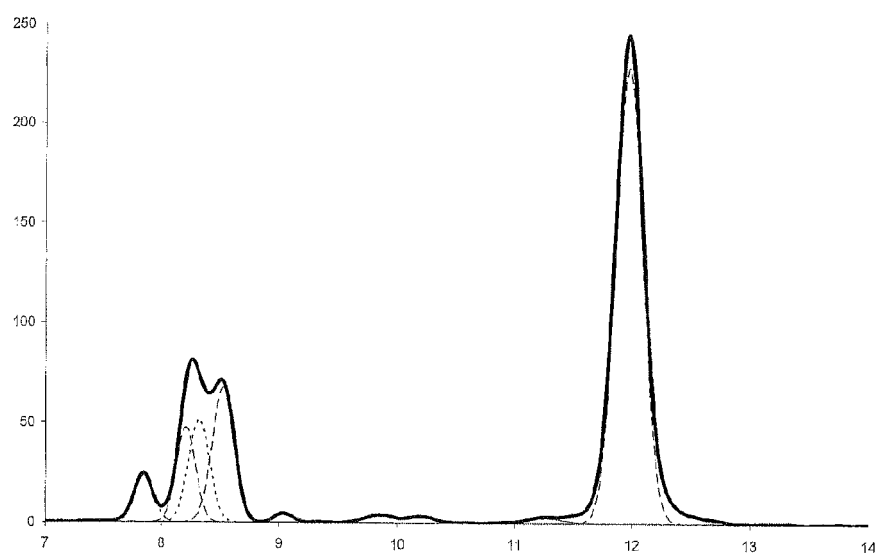
FIG. 4 illustrates an ion mobility spectrum of 20 ppb (parts per billion) of methyl salicylate in nitrogen with the predominant dimer ion at 12 milliseconds and some reactant ions.

The mobility spectra obtained according to aspects of this invention are particularly well resolved and almost completely free of noise. A method of the present invention improves the signal-to-noise ratio, and thus the detection sensitivity, by a factor of five. The mobility spectrum is well suited to be fitted by Gaussian curves, as shown in FIG. 4, even for small signals close to the background. Unlike a square-wave modulation function, the analog modulation provides for the stable operation of the correlation analysis.

The square-wave, i.e., binary, modulated ion currents with the two switching states "on" and "off", which have so far been applied almost exclusively, are changed in an ion mobility spectrometer (in contrast to a time-of-flight mass spectrometer) by the diffusion processes during the drift in such a way that their evaluation, whether by correlation or by Fourier analysis, necessarily suffers from the mixture of binary switch coding and analog signal smearing brought about by the diffusion processes. This disadvantage of previous methods is eliminated by the analog modulation technique.

Although the present invention has been illustrated and described with respect to several preferred embodiments thereof, various changes, omissions and additions to the form and detail thereof, may be made therein, without departing from the spirit and scope of the invention.

What is claimed is:

1. A method for the measurement of the mobility spectrum of ions in an ion mobility spectrometer with an ion source, an ion drift region and an ion detector at the end of the ion drift region, comprising:

a modulation device modulating ion current of the ion source with a continuous analog modulation function whose instantaneous frequency varies across a range of frequencies and whose amplitude is simultaneously modulated;

and correlating in a controller the ion current signal measured at the detector with the modulation function to obtain the mobility spectrum.

2. The method according of claim 1, where the modulation function is a chirp with an amplitude modulation.

3. The method of claim 1, where the instantaneous frequency of the modulation stretches from a lower frequency limit to an upper frequency limit which is selected according to the resolution required.

4. The method of claim 3, wherein the instantaneous frequency starts at the lower frequency limit and increases linearly to the upper frequency limit.

5. The method of claim 3, where the instantaneous frequency is nonlinearly changed between the lower and upper frequency limits.

6. The method of claim 1, where the change of the modulation frequency is extended in such a way that it extends over the measuring period required.

7. The method of claim 1, wherein the modulation device comprises a gating grid located at the start of the ion drift region.

8. A method for the measurement of the mobility spectrum of ions in an ion mobility spectrometer with an ion source, an ion drift region and an ion detector at the end of the ion drift region, comprising:

a modulation device modulating ion current of the ion source, with a continuous analog modulation function being a nonlinear chirp or a wavelet;

and correlating in a controller the ion current signal measured at the detector with the modulation function to obtain the mobility spectrum.

9. A method for the measurement of the mobility spectrum of ions in an ion mobility spectrometer with an ion source, an ion drift region and an ion detector at the end of the ion drift region, comprising:

a modulation device modulating ion current of the ion source, with a continuous analog modulation function whose instantaneous frequency is modulated in a non-continuous way by switching phases during zero crossovers according to a coding;

and correlating in a controller the ion current signal measured at the detector with the modulation function to obtain the mobility spectrum.

* * * * *